(12) United States Patent
Srivastava et al.

(10) Patent No.: US 7,999,937 B1
(45) Date of Patent: Aug. 16, 2011

(54) MICROFLUIDIC DEVICES AND METHODS FOR INTEGRATED FLOW CYTOMETRY

(75) Inventors: Nimisha Srivastava, Goleta, CA (US); Anup K. Singh, Danville, CA (US)

(73) Assignee: Sandia Corporation, Livermore, CA (US)

( * ) Notice: Subject to any disclaimer, the term of this patent is extended or adjusted under 35 U.S.C. 154(b) by 358 days.

(21) Appl. No.: 12/433,156

(22) Filed: Apr. 30, 2009

Related U.S. Application Data (60) Provisional application No. 61/052,892, filed on May 13, 2008.

(51) Int. Cl.
G01N 21/00 (2006.01)
(52) U.S. Cl. ........................................................ 356/338
(58) Field of Classification Search .................. None
See application file for complete search history.

(56) References Cited

U.S. PATENT DOCUMENTS

| | | | |
|---|---|---|---|
| 5,641,457 A * | 6/1997 | Vardanega et al. | 356/73 |
| 6,296,810 B1 * | 10/2001 | Ulmer | 422/82.07 |
| 7,116,407 B2 * | 10/2006 | Hansen et al. | 356/73 |
| 7,502,123 B2 * | 3/2009 | Schmidt et al. | 356/519 |
| 2005/0105077 A1 * | 5/2005 | Padmanabhan et al. | 356/39 |
| 2005/0162648 A1 * | 7/2005 | Auer et al. | 356/318 |

\* cited by examiner

*Primary Examiner* — Gregory J Toatley
*Assistant Examiner* — Juan D Valentin
(74) *Attorney, Agent, or Firm* — Dorsey & Whitney (57) ABSTRACT

Microfluidic devices and methods for flow cytometry are described. In described examples, various sample handling and preparation steps may be carried out within a same microfluidic device as flow cytometry steps. A combination of imaging and flow cytometry is described. In some examples, spiral microchannels serve as incubation chambers. Examples of automated sample handling and flow cytometry are described.

21 Claims, 8 Drawing Sheets

MICROFLUIDIC DEVICES AND METHODS FOR INTEGRATED FLOW CYTOMETRY

CROSS-REFERENCE TO RELATED APPLICATION(S)

This application claims the benefit of U.S. Provisional Application Ser. No. 61/052,892, filed May 13, 2008 entitled "Automated method for analysis of single cells," which application is hereby incorporated by reference in its entirety.

STATEMENT REGARDING RESEARCH & DEVELOPMENT

The United States Government has a paid-up license in this invention and the right in limited circumstances to require the patent owner to license others on reasonable terms as provided for by the terms of contract No. DE-AC04-94AL85000 awarded by the U.S. Department of Energy to Sandia Corporation.

BACKGROUND

Flow cytometry is a technique for analyzing particles in a fluid, as will be understood by those skilled in the art. Briefly, particles are hydrodynamically focused in a stream of fluid. An optical energy source, such as a laser, is directed toward the fluid stream, and one or more detectors are positioned to receive scattered light from the particles, light emitted from fluorescent tags on the particles, or both. The detectors may be positioned both inline with the optical energy source, and at various angles to the optical energy source. Different detectors may be sensitive to different wavelengths of optical energy. By analyzing the signals received from the detectors, information about the physical or chemical properties of the particles may be determined. Histograms and other graphical plots may be generated that may depict particle counts or concentrations of particles containing the fluorescent tags.

Flow cytometry has been used to monitor cell signaling events. For example, a cellular immune response may encompass a variety of cellular events. Phosphorylation and dephosphorylation of intracellular proteins may play a vital role in signaling cascades. Measurement of these types of transitory signaling events may shed light on the timing and degree of immune response. Accordingly, flow cytometry may be used to measure an amount of phosphorylated protein. In particular, phospho-epitope staining has been used to stain cells, labeling the phosphate. In this manner, protein phosphorylation may be measured using flow cytometry techniques.

In order to utilize flow cytometry to monitor a cell signaling event, a number of sample preparation and handling steps may be necessary, including stimulation of the cells with a selected challenge to initiate a cell signaling event. A cell fixation step may then be performed to kill the cells and preserve or "freeze" the cell during a particular time in the cell signaling process. A permeabilization step may then be performed to make the cell membrane permeable. Then, phospho-specific antibodies are introduced into the cell to perform staining. Finally, a variety of washing and buffer steps may be required. Each step proceeds using its own respective lab equipment such as Petri dishes, pipettes, and centrifuge tubes.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known circuits, control signals, timing protocols, software operations, materials, particles, reagents, fluids, samples, labels, and analytes may not have been shown in detail in order to avoid unnecessarily obscuring the described embodiments of the invention.

As generally described above, flow cytometry for cellular analysis may require a variety of sample handling and preparation steps. These steps are often time intensive, and may be performed using large and expensive laboratory equipment. The use of individual sample preparation steps on dedicated equipment limits the ability to accurately control and reproduce flow cytometry analysis, in part because it may be difficult to control contamination of each piece of equipment used, and the use of multiple pieces of equipment may increase the risk of exposure to a user. If any of the equipment becomes contaminated with a different or undesired sample, the results may not be adequately reproducible. The sample handling and preparation steps also may impose unnecessary delay on the analysis as each step is performed in a time-consuming fashion. The process may also limit the ability to capture and analyze a fleeting cellular signaling event. For example, passing a sample between different pieces of laboratory equipment dedicated to stimulating the cells and fixating the cells, may limit the temporal resolution of analysis because a certain amount of time will be required to undertake each of these steps. Because cellular signaling events may be rapid, it could be difficult to obtain the resolution needed to observe the process using flow cytometry if the sample must be prepared using a variety of cumbersome, time-delaying steps.

Figure 1:
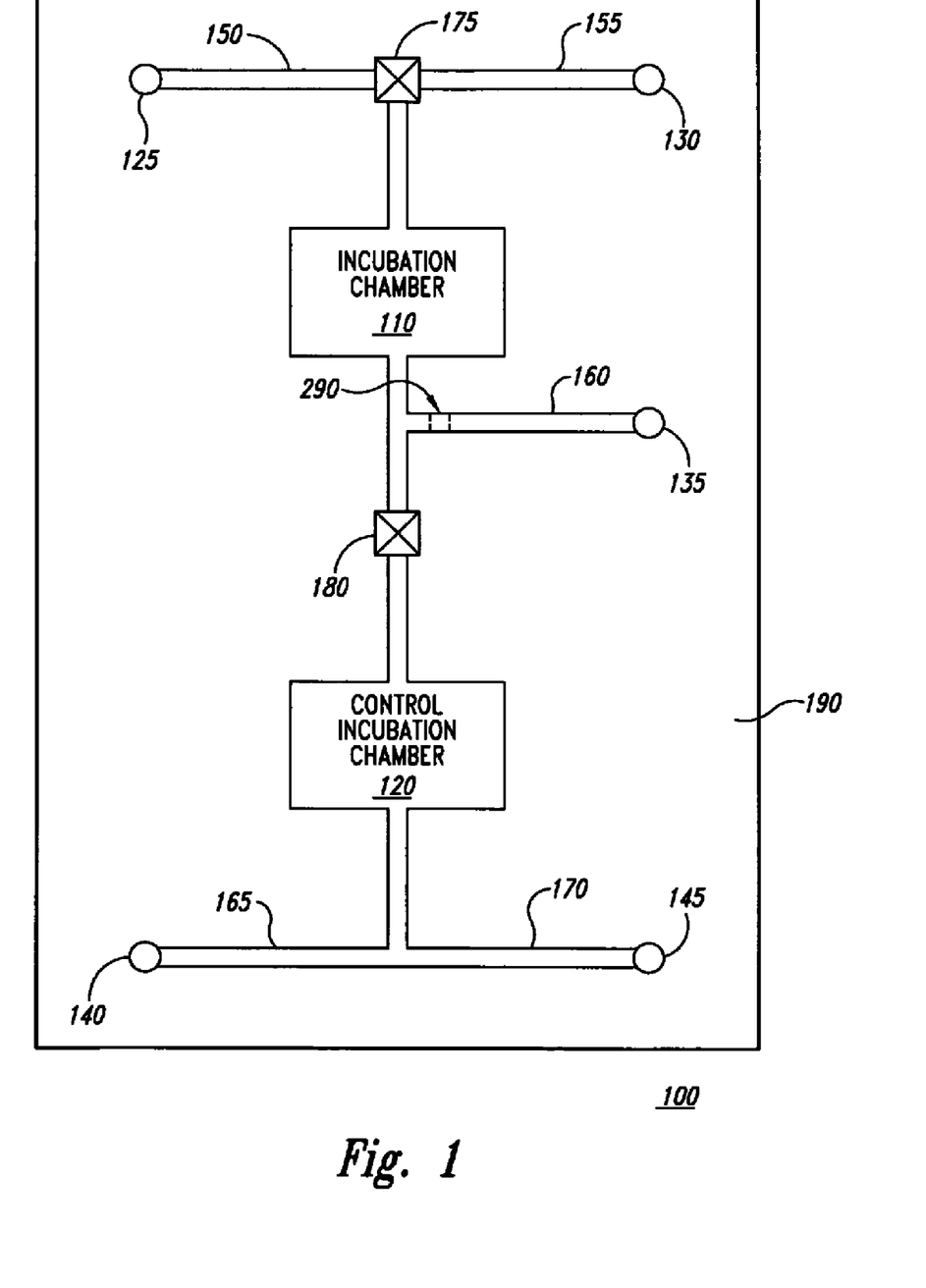
FIG. 1 is a schematic illustration of a microfluidic device, or "chip," 100 according to an embodiment of the present invention.

FIG. 1 is a schematic illustration of a microfluidic device, or "chip," 100 according to an embodiment of the present invention. Microfluidic devices according to embodiments of the present invention generally include a channel having a dimension of around 1 mm or less. In some embodiments, 500 μm or less. In some embodiments, the devices include channels having a dimension of around 100 μm or less. Other dimensions may be used, as generally described below. The microfluidic device 100 includes incubation chamber 110, control incubation chamber 120, inlet/output ports 125, 130, 135, 140, 145, microfluidic channels 150, 155, 160, 165, and 170, and fluidic resistance elements 175 and 180. These elements are generally formed in a substrate 190. While two incubation chambers are shown in FIG. 1, generally any number of chambers may be present, including 1, 2, 3, 4, 5, 6, 7, 8, 9, 10, or more incubation chambers. As will be described further below, one or more of the chambers may serve as a control chamber where particles may not be exposed to a challenge agent.

The substrate 190 may include any of a variety of materials. In some embodiments, as will be further described below, the substrate 190 may be a quartz substrate. Quartz, glass, polycarbonate, fused-silica, PDMS, and other transparent substrates may be desired in some embodiments to allow optical observation of particles within the channels and chambers of the device 100. In some embodiments, however, a plastic, metal or semiconductor substrate may be used. Microscale fabrication techniques, generally known in the art, may be utilized to fabricate the microfluidic device 100. The microscale fabrication techniques employed to fabricate the device 100 may include, for example, etching, surface treatments, photolithography, bonding and other techniques.

The incubation chambers 110 and 120 are provided to contain a volume of sample fluid having particles of interest. As will be described further below, stimulants, stains, buffers, and other reagents, may be introduced to the microfluidic device 100 and interact with the particles in the incubation chambers 110 and 120. The incubation chambers 110 and 120 are shown having a rectangular configuration in FIG. 1; however, substantially any configuration may be used. In particular, as will be described further below, one or more of the incubation chambers 110 and 120 may be implemented as a spiral microfluidic channel. Generally, the incubation chambers 110 and 120 may be sized to contain a sufficient volume of sample fluid for the application of interest. Generally, volumes from 100 to 1000 nL may be used, but other smaller or larger volumes may also be used. In one example, each of the incubation chambers 110 and 120 has a volume of 350 nL. As will be described further below, the incubation chamber 110 may contain particles exposed to a stimulant, while the control incubation chamber 110 may contain particles which have not been exposed to a stimulant, such that they may serve as a control. In other embodiments, the control and challenge experiments may not occur simultaneously, as described in this example. In some embodiments, the control may be run in parallel, such as by conducting a first experiment in one or more incubation chambers of a microfluidic device, then later running control without exposure to the stimulant in one or more of the same incubation chambers (or vice versa). In some embodiments, a control may not be required.

The inlet/output ports 125, 130, 135, 140, and 145, are provided for fluidic access to the microfluidic device 100. While five ports are shown in FIG. 1, generally any number of ports may be provided to facilitate fluid access to and from the microfluidic device 100 at desired locations. Multiple combinations of the inlet/outlet ports can be provided on the device 100. Each combination may allow for a unique analysis on the microfluidic device 100. Although referred to as inlet/outlet ports, each port may be used as an inlet, as an outlet, or may serve a combination of inlet/outlet functions, as will be described further below. The inlet/outlet ports may be coupled to external reservoirs, as will also be described further below. Inlet/outlet ports may have generally any dimension, including from 100 μm to 2 mm in some examples. In one example, the inlet/outlet ports 125, 130, 135, 140, and 145 may have diameters of 500 μm. In some examples, the inlet/outlet ports 125, 130, 135, 140, and 145 may have different diameters.

The microfluidic channels 150, 155, 160, 165, and 170 are provided to route the fluids through the microfluidic device 100. Microchannels used in embodiments of the invention generally may range in dimensions of depth from 1 μm to 1 mm, 1 μm to 500 μm in some embodiments, and 10 μm to 300 μm in other embodiments. The width of the microchannels generally may range from 1 μm to 1 cm, 1 μm to 1 mm in other embodiments, 1 μm to 500 μm in some embodiments, and 10 μm to 300 μm in other embodiments. The width and depth of the microchannel are generally selected to obtain the desired flow characteristics in the channel and provide sufficient volume for the amount of sample or particles to be received by the channel. The length of the microchannels generally may range from 10 μm to 10 cm, from 100 μm to 1 cm in other embodiments. Generally, the length of the microchannel is selected to route fluid the appropriate distance between inlet/outlet ports and chambers, for example. While example dimensions of channels have been provided herein for reference, other dimensions may be used in other embodiments.

The microfluidic channel 170 may also function as a flow cytometry detection area. As will be described further below, sample fluid containing labeled particles may flow from the incubation chambers to the inlet/outlet ports 145, being transported through the microfluidic channel 170. A flow cytometry buffer solution may flow through the microfluidic channel 165 from the inlet/outlet port 140. The flow cytometry buffer fluid may hydrodynamically focus particles as the flow of flow cytometry buffer fluid meets the flow of sample fluid from the incubation chambers. Another set of inlet/outlet ports can be used in conjunction with 140 to produce multidirectional and more efficient hydrodynamic focusing of the particles. The hydrodynamically focused particles may then be analyzed by flow cytometry energy sources and detectors positioned to analyze particles in the microfluidic channel 170.

Fluidic resistance elements 175 and 180 are provided to fluidically isolate the incubation chambers 110 and 120 from each author and from some of the inlet/output ports. The fluidic resistance elements 175 and 180 provide resistance to fluid flow such that, when pressure driven flow is utilized, pressure over a predetermined threshold is necessary to move fluid through the fluidic resistance elements 175 and 180. In this manner, the fluidic resistance elements 175 and 180 may serve as gates for fluid flow. As will be described further below, the fluidic resistance elements 175 and 180 may be implemented as valves, narrower microfluidic channel segments, or generally any other structure providing resistance to fluid flow.

Different components of the microfluidic device 100 have been described above. Use of the microfluidic device 100 to conduct sample handling, sample preparation, microscopy, and flow cytometry, will be described further below. The microfluidic device 100 in FIG. 1 illustrates basic components of a microfluidic device according to an embodiment of the present invention for integrating sample handling, sample preparation, and flow cytometry on a microfluidic device. Another embodiment of a microfluidic device for performing flow cytometry will now be described with reference to FIG. 2.

Figure 2:
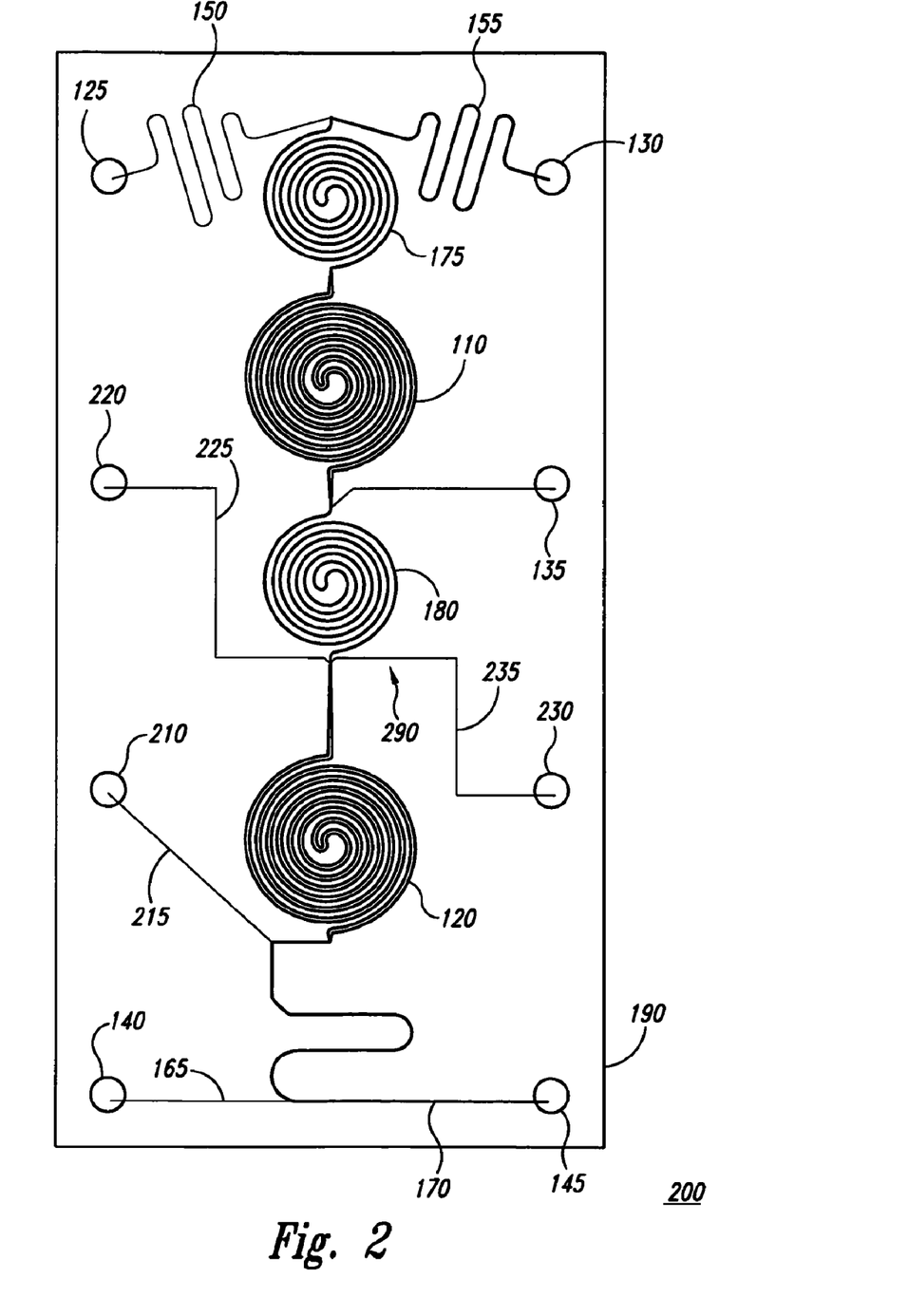
FIG. 2 is a schematic illustration of a microfluidic device, or "chip," 200 according to an embodiment of the present invention including spiral incubation chambers.

FIG. 2 is a schematic illustration of a microfluidic device, or "chip," 200 according to an embodiment of the present invention including spiral incubation chambers. The microfluidic device 200 includes many of the same components as the microfluidic device 100 of FIG. 1, and like reference numbers are used in FIG. 2 to label like components. The incubation chambers 110 and 120 of FIG. 2, however, are implemented as spiral microchannels. The microchannels of the spiral may be sized to achieve desired flow properties, and have a suitable volume for containing a population of particles sufficient for the subsequent flow cytometry analysis. In one example, each of the chambers 110 and 120 may contain 2000 cells when fully loaded, in 350 nL of fluid volume. These numbers are exemplary only, and intended to provide an understanding of the general size and volumetric capacity of the chambers. Other sizes may be used. The spiral configuration may advantageously reduce a dead volume of fluid within the microfluidic device 200.

The fluidic resistance elements 175 and 180 are also implemented as spiral microchannels in FIG. 2. The spiral microchannels of the fluidic resistance elements 175 and 180 may generally have a width that is less than the width of the spiral microchannels forming the incubation chambers 110 and 120, respectively. The smaller width of the spiral microchannels of the fluidic resistance elements 175 and 180 may provide resistance to flow such that pressure driven flow should be driven at a pressure greater than a threshold in order to pass through the fluidic resistance elements 175 and 180. Pressure driven flow driven with less than the threshold pressure may not pass through the fluidic resistance elements 175 and 180. Additional inlet/outlet ports 210, 220, and 230 and microchannels 215, 225, and 235 are provided in the microfluidic device 200 for providing fluid entrance and exit at additional places in the microfluidic device 200 as shown. As shown in FIG. 2, portions of the microchannels 150 and 155, as well as a portion of the microchannel coupled between the incubation chamber 120 and the flow cytometry channel 170, may contain curved portions. The curved portions may generally add length to the microchannel within a same top-down area. In this manner, the length of the microchannel may add greater control of fluidic steps. For example, various flow effects may be observed at the entrance to a microchannel, causing the flow to exhibit non-ideal turbulent or other characteristics. By lengthening the microchannel using, for example, the curved back-and-forth portions shown, flow may be more uniform within the incubation chamber 110 or within the flow cytometry microchannel 170.

Examples of microfluidic devices have been described above that may be used to conduct sample preparation, sample handling, flow cytometry, and microscopy. Example chambers, channels, inlet/outlet ports, and fluidic resistance elements have been described. Other components or variations of these components may also be used. An example of a method for conducting a flow cytometry analysis using the microfluidic device 200 of FIG. 2 will now be described with reference to FIGS. 3 and 4A-4H.

Figure 3:
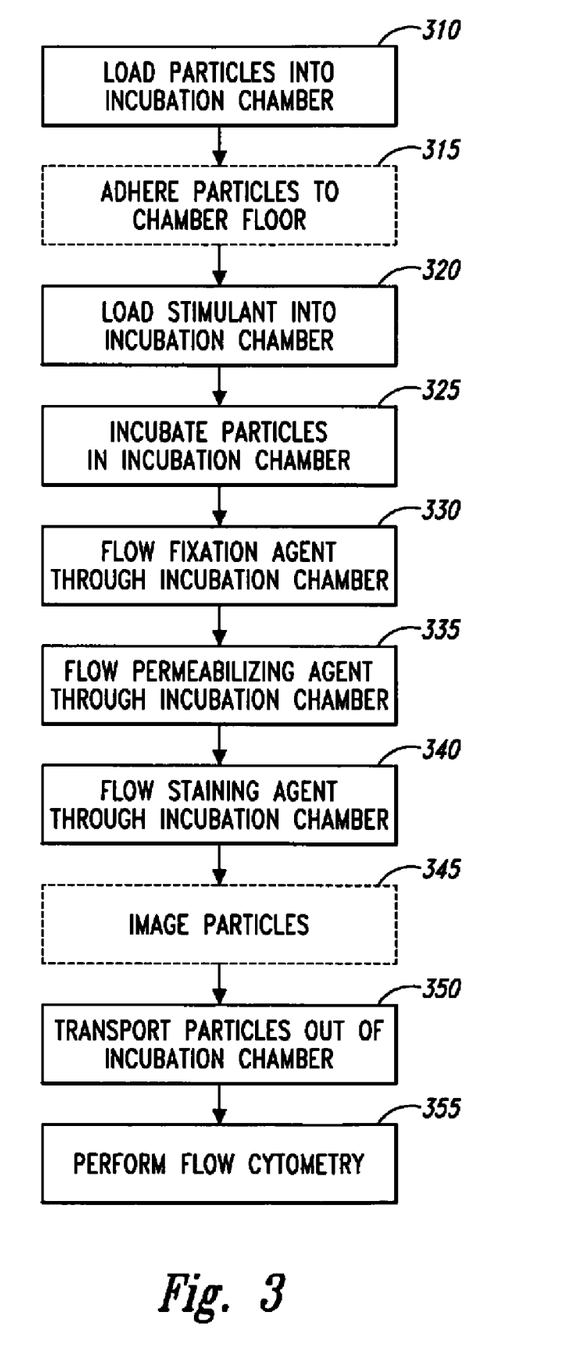
FIG. 3 is a flowchart illustrating blocks of a method for performing a flow cytometry analysis according to an embodiment of the present invention.

FIG. 3 is a flowchart illustrating blocks of a method for performing a flow cytometry analysis according to an embodiment of the present invention. FIGS. 4A-4H are schematic illustrations of the microfluidic device 200 of FIG. 2 illustrating fluid flow during the different blocks of FIG. 3.

In block 310, particles are loaded into the incubation chamber or chambers of the microfluidic device 200. In block 315, the particles may be allowed to settle and adhere to the floor of the incubation chamber or chambers. Settling will be described further below. Settling, adhesion, or both, may not be required in other embodiments. In block 320, a stimulant agent is loaded into an incubation chamber. The stimulant agent may be loaded into only one of the incubation chambers, while particles in a second chamber are used as a control, as described further below. In block 325, the particles are incubated. During incubation, signaling processes or other changes may be occurring in the particles. Following incubation, in block 330, a fixation agent is introduced into the incubation chamber to fixate the particles. The fixation agent generally halts or slows the progress of change occurring during incubation. In block 335, a permeabilizing agent may be introduced into the incubation chamber to permeabilize the particles, such as cells, if desired. In block 340, a staining agent is introduced into the incubation chamber to stain desired portions of the particles, as will be described further below. Once stained, the particles may be imaged in block 345, although imaging may not occur in other embodiments. The particles may be imaged within the incubation chambers, or other portions of the microfluidic device utilizing a suitable microscope positioned to image the device. In block 350, the particles are transported out of the incubation chamber. In block 355, flow cytometry is performed in a microchannel of the microfluidic device coupled to the incubation chamber.

Although not shown explicitly in FIG. 3, a variety of other washing steps may be performed at various times during the method.

Any of a variety of particles may be introduced into the incubation chambers and analyzed according to embodiments of the present invention. Examples of particles of interest include, but are not limited to, cells, including macrophage cells, and beads, including beads having cells or other biological materials attached to the beads. Examples of the present invention may be used to analyze signaling events within cells. That is, as will be described further below, the phosphorylation, dephosphorylation, or both, of particular proteins may be observed using described examples at different points in the cellular signaling process.

The particles are introduced into the device in a fluid suspension. Any of a variety of suitable buffer solutions may be used to form a fluid suspension of particles for loading into the incubation chambers. The particular fluid may be selected based on compatibility with the composition of the microfluidic device and the particles of interest.

In block 320, the particles may be allowed to settle and may adhere to a surface of the incubation chambers 110 and 120. Accordingly, a surface of the incubation chambers 110 and 120 may be formed using a material or treated to be suitable for adhesion with a particle of interest. For example, macrophage cells may be used in an incubation chamber having a quartz surface, and the macrophage cells may generally settle and adhere to the quartz surface. In other examples, a different surface treatment may be used to promote particle adhesion. In other examples, adhesion may not occur, and methods proceed in a different manner, as described further below.

In embodiments utilizing particle adhesion, flow may be stopped for a settling time to allow for particle settling and surface adhesion. Without being bound by theory, the cell settling time may be approximated using a settling velocity (v) for cells in a dilute suspension, which may be given by:

$$v = \left(\frac{2}{9}\right) r^2 (\bullet F) \frac{g}{\mu}$$

where •F is the deviation of the density of particles from that of the media, μ represents the viscosity of the media, r is the average size of a particle (about 10 μm for macrophage cells). Accordingly, in one example where macrophage cells have an F of 1.05 g/mL and the media has an F of 1.01 g/mL, the required settling time may be less than one second. However, a longer settling time may be used to ensure particles have settled appropriately and adhered to an incubation chamber surface. In one example, the settling time is 5 minutes. Although settling and adhesion is described here, in other examples, the particles used, chamber surface, or both, may not be appropriate for particle adhesion to a chamber surface.

Any of a variety of stimulating agents may be used. The stimulating agent will generally initiate a signaling process within the cell reacting to the stimulating agent. Accordingly, generally any stimulating agent initiating a cellular signaling process may be used including, but not limited to, toxins and hormones. In one example, the endotoxin lipopolysaccharide (LPS) may be used as a stimulating agent to initiate a signaling process within macrophage cells.

The particles are incubated with the stimulating agent for an incubation time in block 325. The incubation time may be controlled by a timed incubation interval of stopped flow once the stimulating agent has been introduced to the incubation chamber. Low volumes of the incubation chamber, 350 nL in one example, and applied flow rates of 5 µL/min resulted in rapid fluid exchange of 4 seconds in one example. These numbers are exemplary and intended to demonstrate that the magnitude of chamber volumes attainable, coupled with realistic flow rates, yield possible fluid exchange within the incubation chamber of several seconds. In other examples where the volumes are larger, flow rates slower, or both, a longer fluid exchange interval may occur. The fluid exchange rate may be related to an earliest time point in a signaling process that may be reliably analyzed. That is, in one example, particles may be exposed to a fixation agent approximately 5 seconds after exposure to a stimulating agent within the incubation chamber. This may allow analysis of a signaling pathway starting at approximately 5 seconds following the start of the signaling activity. In other examples, the incubation time may be less than 10 seconds, in other examples less than 30 seconds, and in other examples less than one minute. Other incubation times may also be used including 5 minutes, 10 minutes, 15 minutes, and 30 minutes. The short time periods may be an improvement over systems employing separate sample handling, preparation, and analysis steps and devices which may require a longer time period following stimulant exposure before fixation. In some examples, the flow rates and incubation chamber volumes may be configured such that an incubation period as short as 100 ms may be attainable. While these short stimulation periods may not be appropriate for all systems, short time scale stimulation may be used to monitor signaling components on the relevant time scale, such as short-lived nuclear phospho-proteins (e.g., c-myc protein), cytoplasmic $Ca^{2+}$, aggregation of surface receptors, protein phosphorylation, and subsecond protein oscillations in platelets.

Following incubation, a fixation or "freezing" agent may be flowed through the incubation chambers in block 330. Any suitable fixation agent may be used that generally halts the signaling process initiated by the stimulating agent. In one example, a fixation agent including 2% paraformaldehyde was used.

Following fixation, a permeabilizing agent may be flowed through the incubation chambers to permeabilize cell membranes. Any suitable permeabilizing agent may be used, including but not limited to methanol.

A variety of staining agents may be used. The staining agent selected may generally be selected to stain a target analyte of interest. Any number of target analytes may be stained, including proteins. The staining agent may be tagged with a fluorescent tag for later fluorescent analysis. A wide variety of suitable fluorescent tags are known in the art. The selection of fluorescent tags may be based on the staining agent used, as well as the detectors used, described further below. The detector used may generally be sensitive to a wavelength emitted by the fluorescent tag. As described generally above, embodiments of the present invention may be used to observe the phosphorylation, de-phosphorylation of proteins, receptor-ligand binding, protein expression, protein secretion or a combination of these involved in cellular signaling as well as other non-signaling pathways. Accordingly, staining agents used may include fluorescently tagged phospho-specific antibodies. The antibody may be selected according to the protein of interest, such as ERK1/2 or p38, as will be described further below.

In addition to flow cytometry, particles may be analyzed via imaging, block 345 in FIG. 3, within the incubation chamber. In some embodiments, the particles may be flowed to a different location within the microfluidic device for imaging. As will be described further below, imaging may proceed using a microscope positioned to view particles within the microfluidic device. Accordingly, in some embodiments, all or a portion of the microfluidic device is formed by a material that is at least partially transparent such that the interior/exterior details of the particles may be imaged. Quartz is used in some embodiments. Any suitable imaging technique may be used including confocal microscopy, differential interference contrast (DIC) microscopy, fluorescent microscopy, or combinations thereof. Allowing the particles to be imaged within the same device used to perform flow cytometry may advantageously allow for both imaging and flow cytometry analysis to be performed on a same sample within a short period of time. For example, cells may be imaged within the incubation chamber. The quantity, concentration, or both of stained components of the cells may be visually observed. The cells may then be transported to the flow cytometry microchannel and flow cytometry analysis performed. The imaging step may also be used to confirm particle staining. If particles are not observed as being properly stained, the particles may be transported to a waste reservoir without further analysis, in some embodiments. While the imaging step is shown in FIG. 3 following staining, imaging may also be used to observe particles during or following the completion of any of the other steps—including to observe loading of the particles into the incubation chamber, and settling of particles to a surface of the chamber.

Transporting the particles out of the incubation chamber may occur in any of a variety of ways. In embodiments, where particles have adhered to a surface of the incubation chambers for exposure to the stimulating agent, the particles may be released using a high flow rate purge with a buffer solution. A range of shear rates may be applied to detach particles depending on the nature of the particles, substrate, surface chemistry etc. Flow rates as low as a few nL/s to a few mL/s may be used, although other flow rates may be used in other examples. In other embodiments, other forces may be used to detach cells from a surface of the incubation chamber, such as but not limited to, an enzymatic force.

Particles are hydrodynamically focused for flow cytometry analysis. Hydrodynamic focusing will be described further below, and is generally understood in the art. Throughput of the sample through the flow cytometry channel may be related to the degree of hydrodynamic focusing and size of the channel. In one example, a 10:1 focusing ratio allowed a throughput of around 100 cells per minute. Flow cytometry may be performed according to any suitable flow cytometry methodology, as will be described further below. Generally, energy emission is detected from the stained particles in one or more angles from the direction of energy excitation. Detectors generate a detection signal based on the energy received, and the magnitude of the detection signal may be used to determine a quantity of target analyte present in each particle. In one example where the particles were cells and the target analyte was a phosphorylated protein, the magnitude of the detection signal may be used to establish a degree of phosphorylation in each cell.

Referring now to FIGS. 4A-4H, an example of flow through the microfluidic device 200 of FIG. 2 is shown during the above described method for integrated flow cytometry. Particles are loaded into the incubation chambers 110 and 120 in FIG. 4A. A fluid sample containing the particles enters the microfluidic device 200 through the inlet/outlet port 125 and is driven with sufficient pressure to be transported through both fluidic resistance elements 175 and 180. The fluid containing the particles may flow continuously through the device, exiting at the inlet/outlet port 145. As described above with reference to FIG. 3, once particles have been loaded into the incubation chambers 110 and 120, the particles may in some examples be allowed to settle and may adhere to one or more surfaces of the incubation chambers 110 and 120, such as the floor. In other embodiments, the cells may be retained in the incubation chambers 110 and 120 by another mechanism, such as a filter.

Figure 4A:
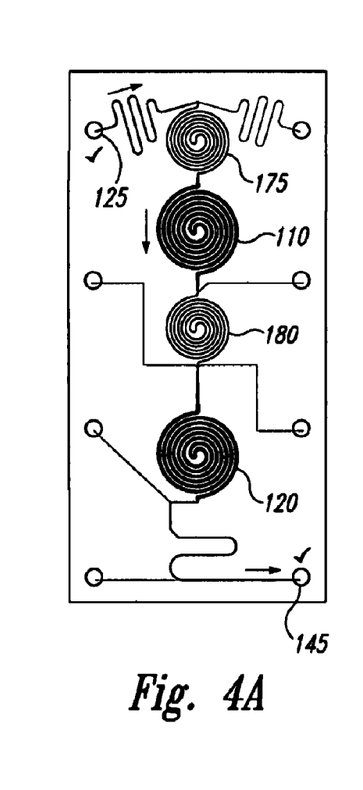
FIGS. 4A-4H are schematic illustrations of the microfluidic device 200 of FIG. 2 illustrating fluid flow during the different blocks of FIG. 3.
Figure 4B:
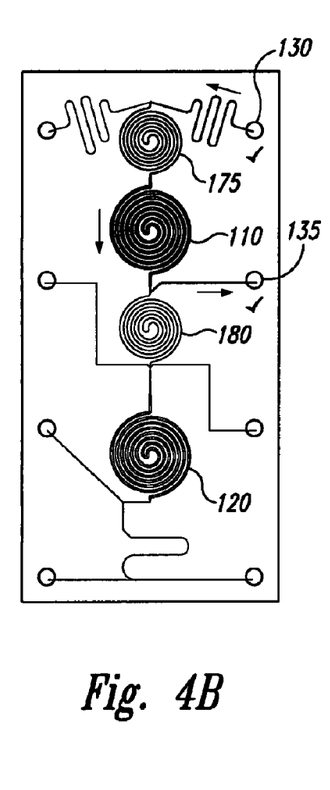

Referring now to FIG. 4B, a stimulant may be loaded into the incubation chamber 110 by entering the inlet/outlet port 130 and exiting the inlet/outlet port 135. In the example of FIG. 4B, the fluidic resistance of the path to the inlet/outlet port 135 is less than the resistance imposed by the fluidic resistance element 180. Accordingly, the stimulant is flowed through the incubation chamber 110 but not the incubation chamber 120. In this manner, the particles in the incubation chamber 120 may serve as control particles that have not been exposed to the stimulant.

Figure 4C:
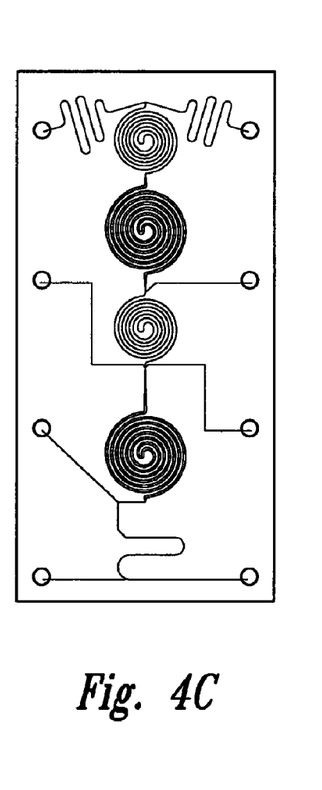

Referring now to FIG. 4C, following stimulant exposure, the particles are allowed to incubate. During the incubation time, fluid may not flow through the microfluidic device 200. Rather, the particles are simply allowed to incubate in a stationary fluid solution.

Figure 4D:
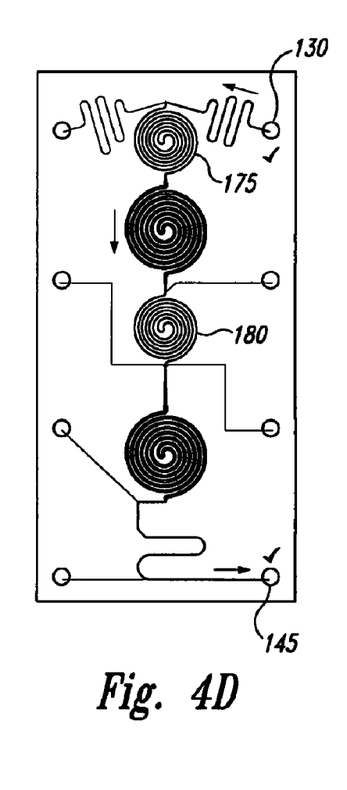

Referring now to FIG. 4D, following incubation, a fixation agent may be flowed through microfluidic device, from the inlet/outlet port 135 to the inlet/outlet port 145, as shown. In this manner, the fixation agent may flow through both fluidic resistance components 175 and 180 and both incubation chambers 110 and 120. Accordingly, particles in both chambers 110 and 120 may be fixated. As generally described above, exposure to the fixation agent may kill cells in the incubation chambers, halting the signaling process at a particular stage in the signaling cascade, and allowing subsequent imaging and flow cytometry analysis of that stage, as will be described further below. Following fixation, additional agent may be flowed through the microfluidic device in the manner indicated in FIG. 4D, including permeabilizing agents, and staining agents, as generally described above.

Figure 4E:
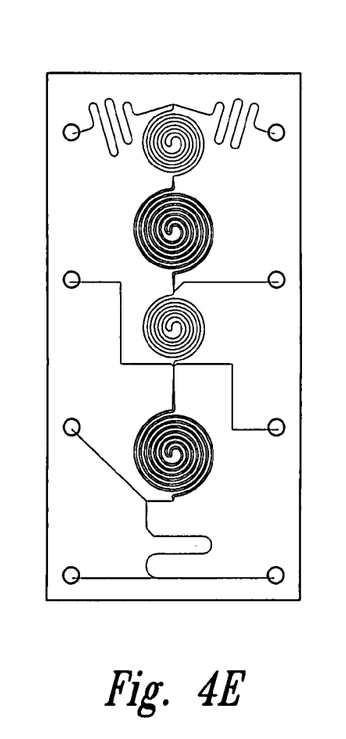

Referring now to FIG. 4E, following introduction of a staining agent to the microfluidic device, the particles may again be allowed to incubate in a stationary fluid.

Figure 4F:
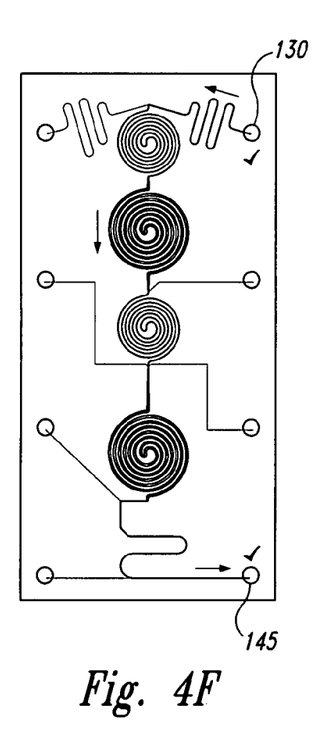

Following incubation with the staining agent, referring to FIG. 4F, a wash step may be performed. A washing agent may be flowed through the microfluidic device from the inlet/outlet port 130 to the inlet/outlet port 145. The washing agent may remove extraneous staining agent or other agents remaining within the microfluidic device whose presence may disrupt subsequent imaging or flow cytometry.

Figure 4G:
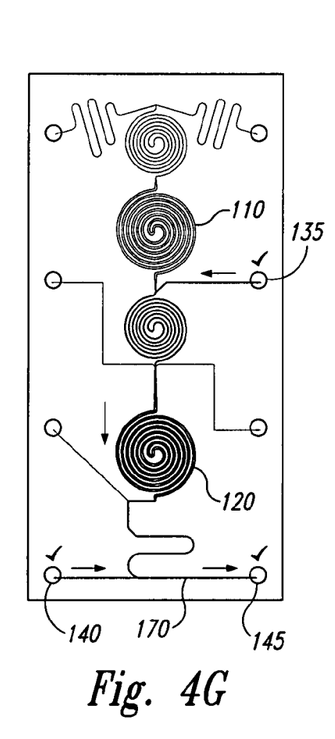

Flow cytometry proceeds by transporting particles first from the control incubation chamber 120, and then from the incubation chamber 110. Referring to FIG. 4G, particles are transported out of the control incubation chamber 120 by flowing a buffer fluid through the microfluidic device from the inlet/outlet port 135 to the inlet/outlet port 145 at a sufficient rate to generate shear forces sufficient to detach the particles from the surface of the incubation chambers 110 and 120. A flow cytometry buffer fluid is flowed through the microfluidic device from the inlet/outlet port 140 to the inlet/outlet port 145. The flow cytometry buffer fluid may hydrodynamically focus the particles within the flow cytometry microchannel 170 for flow cytometry analysis. Following transport of the particles from the control incubation chamber 120 through the flow cytometry microchannel 170 and out the inlet/outlet port 145, particles remain in the incubation chamber 110.

Figure 4H:
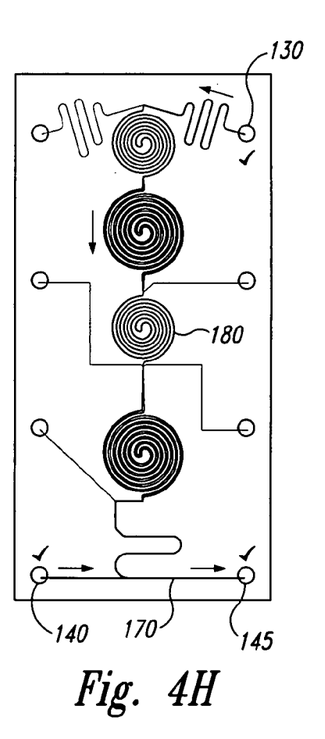

Referring now to FIG. 4H, particles are transported out of the incubation chamber 110 by flowing a buffer fluid through the microfluidic device from the inlet/outlet port 130 to the inlet/outlet port 145. The particles from the incubation chamber 110 pass through the fluidic resistance element 180 and the control incubation chamber 120 before reaching the flow cytometry microchannel 170. Flow cytometry buffer fluid flows through the microfluidic device from the inlet/outlet port 140 to the inlet/outlet port 145 to hydrodynamically focus the particles in the flow cytometry channel 170.

Accordingly, examples have been described above of methods for conducting a flow cytometry analysis and sample handling and preparation steps using a microfluidic device. The examples described above may include particle settling and adhesion to an incubation chamber surface as a method of immobilizing the particles within the incubation chamber for exposure to a stimulating agent and other steps. Adhered particles may later be released using a high flow rate purge. These methods may be suitable for adherent particles and surfaces, such as macrophage cells on quartz, for example. However, in other examples, the particles may not adhere to an incubation chamber surface. Accordingly, other methods for retaining the particles in the incubation chamber region may be used, as will now be described with reference back to FIG. 2 and FIGS. 4A-4H.

To accommodate nonadherent particles, a polymer filter may be positioned in a microchannel within the microfluidic device to contain particles within the incubation chamber during subsequent washing and reagent delivery steps. For example, referring back to FIGS. 1 and 2, a porous gel 290 may be positioned in the microchannel 160 of FIG. 1 or the microchannel 235 of FIG. 2, between the incubation chambers 110 and 120. The polymer filter may generally fill the cross-sectional area of the microchannel, and may have any length. The polymer filter can be positioned in one of the several inlet/outlet ports. In one example, the microchannel had a 90 µm width, and the porous gel 290 also has a 90 µm width and a 250 µm length.

The polymer filter may be fabricated using any of a variety of methods. In one example, phase-separation photopolymerization may be used. The pore-size of the filter may be controlled during this process, and the pore size is generally selected such that the polymer filter may prevent particles of interest from passing. In one example, macrophage cells having a diameter of 10 µm are used, and the filter is constructed with a pore size of 4 µm.

During fluid exchange, such as the introduction of stimulating agents, fixation agents, permeabilizing agents, and wash fluids, particles may be drawn toward the polymer filter using a vacuum applied downstream of the polymer filter. Particles may then stack up at the filter interface while liquid is drawn through the pores. Once reagent exchange is complete, particles may be released from the filter interface using a pressure pulse. Collection and release of particles at the filter interface may be repeated for each fluid exchange step. In some examples, multiple polymer filters may be provided in one or more side channels of the microfluidic device for redundancy in the event any single polymer filter is compromised.

When a polymer filter is used in this manner to retain nonadherent particles during fluid exchange, it may not be feasible to run both an experimental and a control assay in the two incubation chambers of the device, as the control and experimental particles may not be isolated from one another. Instead, the experimental and control assays may be run sequentially one after the other, and the microfluidic device washed between assays.

Examples of methods of performing flow cytometry, including sample handling and preparation steps, within a microfluidic device have been described above. As may be appreciated, the methods include flowing various fluids through a microfluidic device, in some examples utilizing different combinations of inlet/outlet ports. In some examples, the microfluidic device may be coupled to a flow controller and manifold for automated fluid delivery. Examples of systems including automated flow controller will be described below. The flow controller may be programmably configured to control intervals of continuous and stopped flow within all, or portions of, the microfluidic device. An example is described below utilizing reservoirs, fluid manifolds, and valves that are external to the microfluidic device. In other examples, however, combinations of the valves, fluid reservoirs, and associated fluidic connections, may be integrated within the microfluidic device.

Figure 5:
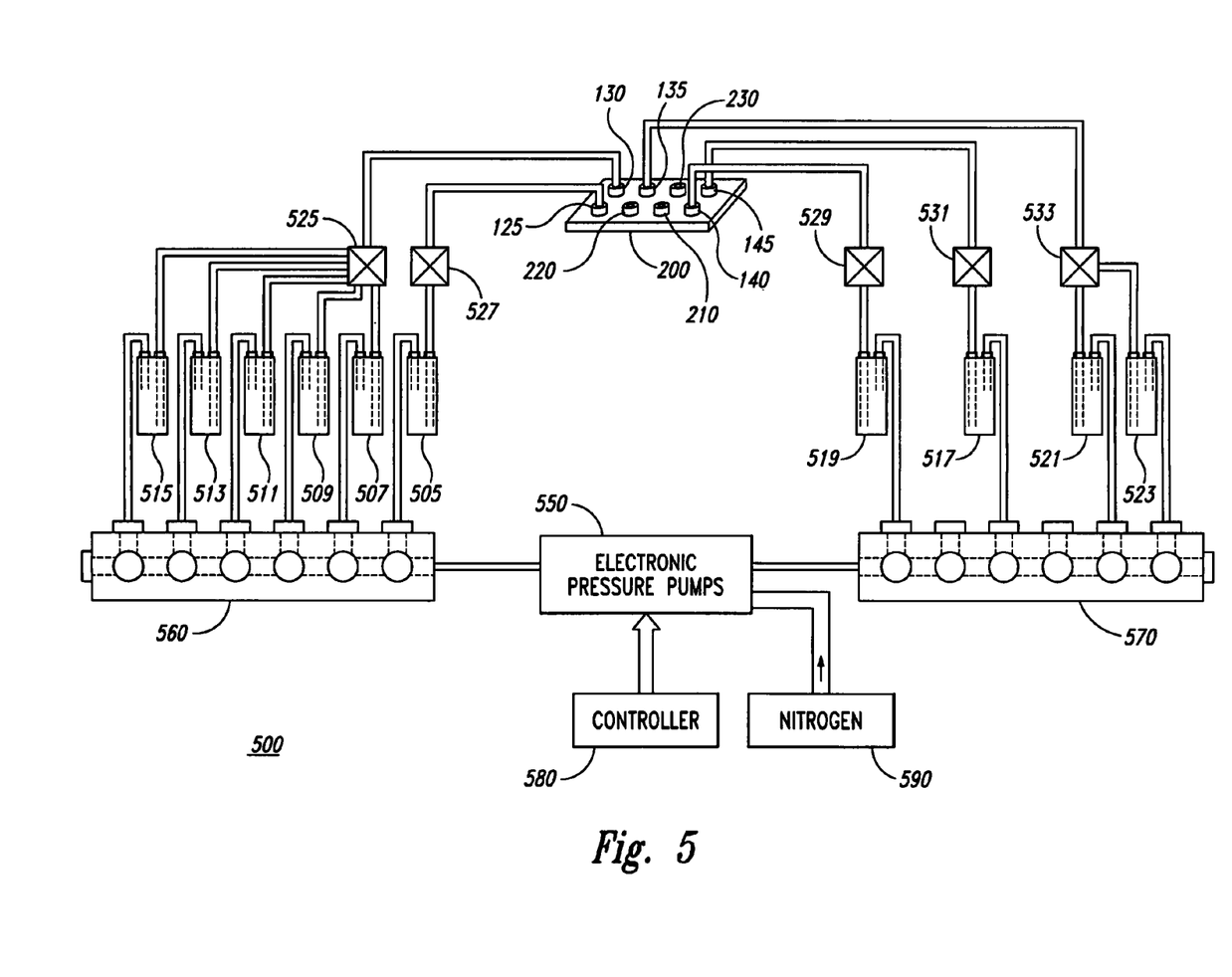
FIG. 5 is a schematic illustration of a system 500 according to an embodiment of the present invention.

FIG. 5 is a schematic illustration of a system 500 according to an embodiment of the present invention. The system 500 includes the microfluidic chip 200, described above with reference to FIG. 2. The inlet/outlet ports 125, 130, 135, 140, 145, 210, 220, and 230 are shown. The inlet/outlet ports are coupled to reservoirs using respective tubing. As an example, reservoirs 505, 507, 509, 511, 513, 515, 517, 519, 521, and 523 are coupled to the microfluidic chip 200 utilizing tubing and valves 525, 527, 529, 531 and 533. As shown, some valves couple a single reservoir to a single inlet/outlet port, while other valves (such as the valve 525) couple multiple reservoirs to a single inlet/outlet port. The reservoirs are coupled to fluid manifolds 560 and 570. Electronic pressure pumps 550 are coupled to the fluid manifolds 560 and 570. A controller 580 is coupled to the electronic pressure pumps 550. A nitrogen gas supply 590 is coupled to the electronic pressure pumps 550 to generate the pressure to be applied by the electronic pressure pumps 550. Gases other than nitrogen may also be used.

Generally, any type of fluid connectors may be used to couple the tubing to the microfluidic device 200. In one example, plastic Tube-tite connectors were used. In some examples, the microfluidic chip 200 may be placed in a housing and sealed using O-ring connectors, and the tubing coupled to the housing.

Generally, any type of tubing may be used. In some examples, plastic tubing having a diameter of less than 500 µm, in one example 125 µm, may be used. The diameter of the tubing may be selected to reduce cell loss by axial dispersion in the tubing. In some examples, different diameter tubing may be connected to different inlet/outlet ports depending on the function of the port.

Electronic pressure pumps 550 may be coupled to the fluid manifolds 560 and 570 for control of pressure applied to the reservoirs 505, 507, 509, 511, 513, 515, 517, 519, 521, and 523. The fluid manifolds 560 and 570 may have manual controls, as depicted, for opening or closing a connection between the electronic pressure pumps 550 and the reservoirs. In some embodiments, all reservoirs that may be used have an open connection to the electronic pressure pumps 550, and pressure is applied to all input reservoirs simultaneously. Fluid flow through the microfluidic device may then be initiated by opening a valve between a pressurized reservoir and the microfluidic device. In some embodiments, waste reservoirs have a closed connection between the fluid manifold and the electronic pressure pump, or may not be coupled to the pressure pump. The pressure supplied by the electronic pressure pumps 550 may vary according to the step of the process underway, the microfluidic device geometries, and the composition of the fluids and particles used. In some examples, pressures may be applied up to about 5 psi. Higher or lower pressures may also be applied.

The controller 580 may be coupled to the electronic pressure pumps and the valves 525, 527, 529, 531 and 533 for controlling the applied pressure and valve state. That is, the controller 580 may control fluid flow through the microfluidic device by opening and closing particular valves and setting a pressure level. Multi-input valves, such as the valve 525, may be controlled to select a particular reservoir for connection to the microfluidic device 200.

An example of the control provided by the controller 580 to achieve the flow sequence described above with reference to FIGS. 4A-4H will now be described with reference to the reservoirs and valves of FIG. 5. To initiate sample flow containing particles into the device (FIG. 4A), the controller 580 may apply a control signal to the valve 527 to open the connection between the reservoir 505 containing the sample, and apply a control signal to the valve 531 to open a connection to the waste reservoir 517. Applying a pressure to the sample containing reservoir 505 may result in the flow depicted in FIG. 4A. The controller 580 may be programmed to apply pressure driven flow in this configuration for a predetermined amount of time (a sample loading time).

Following sample loading, as described above, adherent particles may be allowed to settle and adhere to a surface of the incubation chambers. Accordingly, the controller 580 may be configured to stop the pressure applied by the electronic pressure pumps 550, to close the valve 527, or both, to attain stagnant flow for settling. The controller 580 may provide this stagnant flow for a predetermined amount of time (a settling time).

To introduce the stimulating agent as shown in FIG. 4B, the controller 580 may apply a control signal to the valve 525 to open a connection between the inlet/outlet port 130 and the reservoir 507 containing the stimulating agent. The controller 580 may also apply a control signal to the valve 533 to open a connection between an intermediate waste reservoir 521 and the inlet/outlet port 135. In some embodiments, the intermediate waste reservoir 521 may not be needed, and the waste reservoir 517 may be coupled to the valve 533 for this purpose. A suitable pressure is applied by the electronic pressure pumps 550 to achieve the flow of stimulating agent depicted in FIG. 4B. This flow may be continued for a predetermined amount of time (a stimulating time). As generally described above, the amount of time needed to fill the chamber 110 with the stimulating agent may be related to the volume of the chamber and the flow rate, and may affect a minimum elapsed time before the particles may be fixated and analyzed.

Following introduction of the stimulating agent, as generally described above, the particles may be incubated (FIG. 4C). Accordingly, the controller 580 may couple a control signal to the electronic pressure pumps 550 to stop applying pressure, or close the valve 525, or both, to attain stagnant flow for incubation with the stimulating agent. The stagnant flow may be allowed for a predetermined time (an incubation time).

Following incubation, a variety of preparation steps may be performed, as generally described above, including fixation, permeabilization, staining, and washing. To attach the flow shown in FIGS. 4D and 4F, the controller 580 may couple a control signal to the valve 525 to open a connection between the relevant reservoir and the inlet/outlet port 130, and couple a control signal to the valve 531 to open a connection to the waste reservoir 517. A suitable pressure may be applied by the electronic pressure pumps 550, under control of the controller 580 to drive the appropriate flow. Following any of the steps, and in particular, following introduction of the staining agent, stagnant flow may be applied by removing the pressure, closing the valves, or both for a predetermined time (an incubation time).

To empty the control chamber 120 for flow cytometry analysis, the controller 580 may couple a control signal to the valve 533 to open a connection between a buffer reservoir 523 and the inlet/outlet port 135, a control signal to the valve 529 to open a connection between a flow cytometry buffer reservoir 519 and the inlet/outlet port 140, and a control signal to the valve 531 to open a connection to the waste reservoir 517. The pressure applied with the pressure pumps 550 may be sufficient to detach particles from a surface of the chamber 120 where surface adhesion had been used. Flow may continue in this manner for a predetermined period of time (a detection time) while flow cytometry detection is performed in the flow cytometry channel 170.

To empty the incubation chamber 110 for flow cytometry analysis, the controller 580 may close the valve 531 and couple a control signal to the valve 525 to open a connection between a buffer reservoir 515 and the inlet/outlet port 130. Again, the pressure applied with the pressure pumps 550 may be sufficient to detach particles from a surface of the chamber 110 where surface adhesion had been used. Flow may continue in this manner for a predetermined period of time (a detection time) while flow cytometry detection is performed in the flow cytometry channel 170.

While the above example has described automated control by the controller 580, in other embodiments some or all of the steps, such as opening and closing valves, or fluid manifold connections, may be performed manually. In some examples, rather than coupling several reservoirs to a single valve, a single reservoir may be coupled to the valve, and different reservoirs may be manually swapped during operation.

Figure 6:
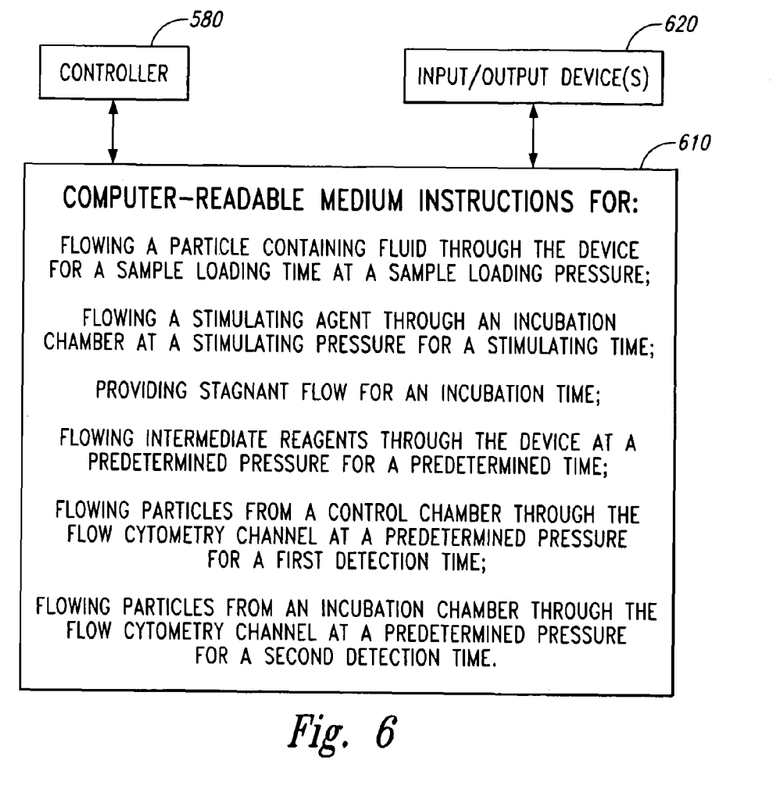
FIG. 6 is a schematic illustration of a computer readable medium according to an embodiment of the present invention.

FIG. 6 is a schematic illustration of a computer readable medium according to an embodiment of the present invention. The computer readable medium 610 may be coupled to the controller 580 and may store instructions for executing the fluid flow steps described above. One or more input or output devices 620 may be coupled to the controller 580, computer readable medium 610, or both, for programming the controller 580. In particular, the computer readable medium 610 may store instructions for flowing a particle containing fluid through the device for a sample loading time at a sample loading pressure, and flowing a stimulating agent through an incubation chamber at a stimulating pressure for a stimulating time. Instructions may further be stored for providing stagnant flow for an incubation time and flowing intermediate reagents (such as fixation, permeabilization, staining, and wash agents, described above) through the device at a predetermined pressure for a predetermined time. Instructions may further be stored for flowing particles from a control incubation chamber through the flow cytometry channel at a predetermined pressure for a first detection time, and flowing particles from an incubation chamber through the flow cytometry channel at a predetermined pressure for a second detection time.

In this manner, the controller 580 may contribute to a completely automated flow cytometry analysis utilizing the microfluidic chip 200. With a suitable reservoir and valve setup, the controller 580 may be programmed to conduct different intervals of continuous and stopped flow, applying the appropriate reagents to the appropriate ports of the device.

Figure 7:
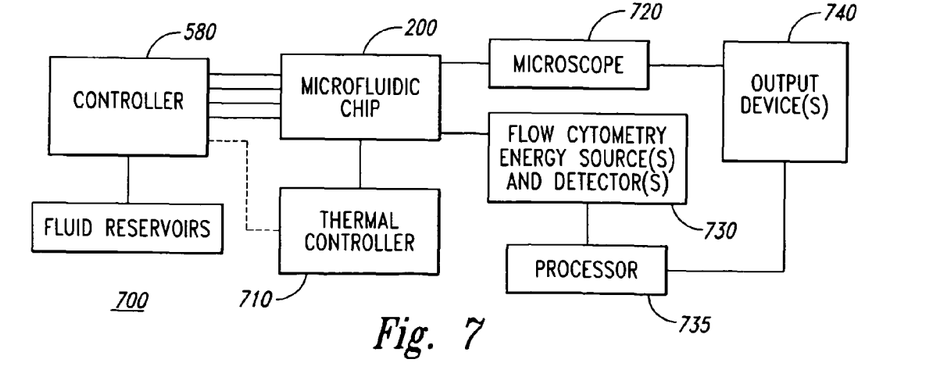
FIG. 7 is a schematic illustration of a system according to an embodiment of the present invention.

FIG. 7 is a schematic illustration of a system 700 according to an embodiment of the present invention. The system 700 includes the microfluidic chip, described above with reference to FIG. 2, the controller 580 and reservoirs 505, 507, 509, 511, 513, 515, 517, 519, 521, and 523 described above with reference to FIGS. 5 and 6. The system 700 further includes a thermal controller 710, a microscope 720, flow cytometry energy sources and detectors 730, and output devices 740.

The thermal controller 710 is coupled to the microfluidic chip 200 and may control the temperature of the microfluidic chip 200. Any type of thermal controller may be used, such as but not limited to, a hot plate. In some embodiments, the thermal controller 710 may be integrated with the microfluidic chip 200, using microfabricated heaters, for example. The thermal controller 710 controls the temperature of the microfluidic chip 200. In some examples, the thermal controller 710 may also be coupled to the controller 580 for automated control of the temperature of the microfluidic chip 200. The desired temperature for the microfluidic chip 200 may depend on a variety of factors, including the process underway within the microfluidic chip, the materials of the microfluidic chip, and the particles, agents, and fluids used. In some examples, a temperature sensor may be integrated with the thermal controller 710 to provide temperature feedback from the microfluidic device 200. In other examples, a temperature sensor may be positioned to sense the temperature of the microfluidic device 200 and be coupled to the thermal controller 710 to provide feedback. In some examples, a temperature sensor may be integrated into the microfluidic device 200.

The microscope 720 is positioned to image particles within the microfluidic chip 200, as generally was described above. Any type of microscope may be used, including, but not limited to an inverting microscope, or a confocal microscope.

Flow cytometry energy sources and detectors 730 may be positioned to conduct flow cytometry analysis in a portion of the microfluidic chip 200, as generally described above. Generally, any number of energy sources and detectors may be used, depending on the flow cytometry analysis, as will be understood in the art. The selection of energy source wavelength and detector sensitivity may be based in part on the type of staining agent used, and the detection methodology. In one embodiment, a laser is used as an excitation source having emission at 488 nm. Optical energy emitted from the hydrodynamically focused stream of stained particles may be detected by one or more detectors. Detectors may be positioned to receive both the forward energy in the direction of the energy source illumination, and scatter energy at an angle from the direction of energy source illumination, as is understood in the art of flow cytometry. Any type of optical energy detector may generally be used, including one or more photomultiplier tubes. Filters may be placed between the microfluidic device and the energy detectors. The detectors generate a detection signal corresponding to the presence or quantity of the staining agent, or both.

A processor 735 is coupled to the flow cytometry energy sources and detectors 730 and may be configured to receive detection signals from the flow cytometry detectors. The processor 735 may then process the detection signals, for example, by fitting peaks to the detection signal or generating population histograms.

One or more output devices 740 may be coupled to the processor 735, the microscope 720, or both. The output devices 740 may display images of the particles based on data received from the microscope 720. The output devices 740 may display, store, or both, the flow cytometry data generated by the processor 735. For example, an output device may display plots of flow cytometry data. As will be appreciated by those skilled in the art, a variety of manipulations of the flow cytometry data may be performed, including but not limited to peak fitting.

Microfluidic devices, systems, and methods for flow cytometry analysis including sample preparation and handling, have been described above. These examples may advantageously allow characterization of intracellular signaling as well as non-signaling processes at the single-cell level. The small fluid volumes needed by the microfluidic device as well as the rapid pace of experiments facilitated in part by the small volume and by the automated fluid handling in some embodiments, may be well suited to the monitoring of numerous time points in a large experimental parameter space that is generally advantageous for signaling studies. That is, because only a small fluid volume is required, and experiments can be conducted quickly, a large number of experiments are feasible covering numerous time points in a particular signaling pathway. Small volumes may also reduce the amount of expensive reagents and potentially scarce sample that is needed for analysis. Furthermore, using automated flow control, the time of fixation may be programmably controlled.

Further, devices and methods according to embodiments of the present invention may advantageously reduce particle loss during flow cytometry. In part because the sample preparation steps (such as stimulation, fixation, and permeabilization) may be performed within the same microfluidic device as flow cytometry, particles are less likely to be lost than if they had been transported from one sample handling device to a second flow cytometry device, or had been transferred between multiple sample handling devices. Cell losses of around 75 percent may be found in macroscale protocols involving chemical permeabilization. In contrast, cell loss may be negligible in embodiments of the present invention. Similarly, embodiments of the present invention may advantageously reduce the amount of particle aggregation that occurs. Particle aggregation occurs when the particles clump together. The aggregation can obscure flow cytometry results.

Devices and methods according to embodiments of the present invention may advantageously reduce an amount of time required to perform each flow cytometry analysis. After stimulation, examples of methods according to the present invention may complete cell handling and flow cytometry analysis within 30 minutes, compared with about 120 minutes for conventional benchtop preparation. The shorter time required may yield more efficient analysis and potential for high-throughput signaling studies.

Embodiments of the present invention may also eliminate or reduce a need for centrifuge-based particle washing required for benchtop studies. Instead, embodiments of the present invention employ polymer filters for nonadherent particles and stopped flow and settling for adherent particles, described above. By eliminating or reducing centrifugation steps, particle clumping, disintegration, and particle loss may be reduced.

Embodiments of the present invention further provide a contained device having a small footprint suitable for use in a space limited facility, or a facility having a heightened bio-safety level. For reagents or samples posing a safety hazard, devices and methods of the present invention may allow minimal user exposure to risk agents, with an enclosed system having no aerosol generation.

From the foregoing it will be appreciated that, although specific embodiments of the invention have been described herein for purposes of illustration, various modifications may be made without deviating from the spirit and scope of the invention. A detailed example is provided below for aid in understanding. The detailed example should not be used to limit the claims to the details described.

EXAMPLE

Utilizing a microfluidic device, system, and method according to an example of the present invention, a murine macrophase cell line (RAW 264.7) was exposed to lipopolysaccharide (LPS). The endotoxin LPS is a component of Gram-negative pathogenic bacteria (e.g., *Tersenia pestis* and *Francisella tularensis*) and induces activation of macrophages through TLR4. Upon activation, TLR4 triggers a signaling cascade that includes phosphorylation of protein kinases ERK and p38. This cascade induces the expression of immune activation genes that may steer the course for immediate defense against pathogen invasion. Such immediate molecular events associated with innate immune response may be categorized as "first responders" and may occur within a few seconds to minutes after stimulation. Accordingly, fine temporal resolution may be needed to analyze these molecular events. This example describes the use of a microfluidic device as described above to monitor phosphorylation of two proteins in the TLR4 pathway—extracellular signal-regulated kinase (ERK1/2) and p38.

The RAW 264.7 murine macrophase cell line was purchased from ATCC® and used for this example. Macrophages were cultured in growth medium consisting of 450 mL of DMEM, 50 mL of FBS (gemcell), 5 mL of HEPES, 5 mL of L-glutamine (200 mM), and 1:100 penicillin/streptomycin. A $5 \times 10^6$ cells/mL cell suspension was used to load cells onto the microfluidic chip.

A quartz microfluidic chip was used as described above with reference to FIG. 2. The microfluidic chip was mounted on a thermoelectric hot plate and integral controller. A temperature sensing thermistor was attached to the quartz chip to provide temperature feedback.

A 15 mW argon ion laser having emission at 488 nm was used as a flow cytometry excitation energy source. A series of adjustable mirrors and a 60× air objective for epifluorescence illumination was used to introduce the laser beam onto the microfluidic device's flow cytometry channel. Emitted energy from the hydrodynamically focused stream of cells was collected through two fluorescence filter cubes with a dichroic mirror and associated emission filters. Collected light from each filter cube was relayed to two photomultiplier tubes (PMT), and the PMT gain tuned using an associated controller. The scatter signal from an optical fiber positioned on a top surface of the microfluidic device was relayed to a third PMT. Resulting data was analyzed using the Peak Finder application in LABVIEW® to construct population histograms of the time-resolved phosphorylation assays. The Peak Finder program fits the peak of the raw signal traces from the PMT with a polynomial fit and returns the peak amplitude and width. Amplitudes of the peak were used to display histograms in MATLAB®.

An inverted microscope was used to capture bright field, epifluorescence and phase contrast images at 10× and 40× magnification.

A cell suspension was loaded into the incubation chambers of the microfluidic device, as generally described above. Approximately 2000 cells were localized in each of the two incubation chambers. The incubation chambers were visually assessed to ensure complete loading. Once the incubation chambers were loaded, the loading flow was stopped and cells were observed as they settled for a 5 minute settling interval. Subsequent shear flow assays indicated the macrophase cells adhered to the quartz channel floor with a force exceeding 1.7 nN.

Following cell adhesion, stimulation was initiated by flowing 10 μM or 1 μM E. coli LPS through the first spiral incubation chamber, as generally described above. The microfluidic device temperature was maintained at 37° C. The second chamber was used for negative control assays, and did not receive LPS. Following a timed LPS exposure (5 second, 5 minute, 10 minute, 15 minute, and 30 minute stimulation intervals were used), a chemical fixative (2% paraformaldehyde) was introduced into both spiral incubation chambers. After fixation, the two spiral incubation chambers were flushed with methanol to permeabilize cell membranes. Numerous programmed intermediate buffer exchanges were conducted to limit cross-contamination. In postpermeabilization, the cells were incubated with fluorescently tagged phospho-specific antibodies to label the phosphorylated epitopes of p38 and ERK 1/2.

Following phospho-staining, immobilized cells were investigated using epi-fluorescence and bright-field microscopy. Intracellular localization of phosphorylated ERK1/2 and p38 was observed in LPS challenged cells. Localization was characterized by high fluorescence signal centralized to the cell nucleus. No phosphorylation of ERK1/2 or p38 was detected via fluorescence microscopy in the control incubation chamber.

After imaging, the immobilized cells were released from the incubation chambers using a high flow rate purge with a trypsin-containing buffer. The cell suspension was hydrodynamically focused and on-chip flow cytometry performed. A 10:1 focusing of the sample flow enabled throughput of 100 cells/min. Less than 10 μL of sample volume was required for the analysis. The magnitude of fluorescence signal detected by the flow cytometry detectors was used to establish the degree of protein phosphorylation in each cell detected.

Figure 8A:
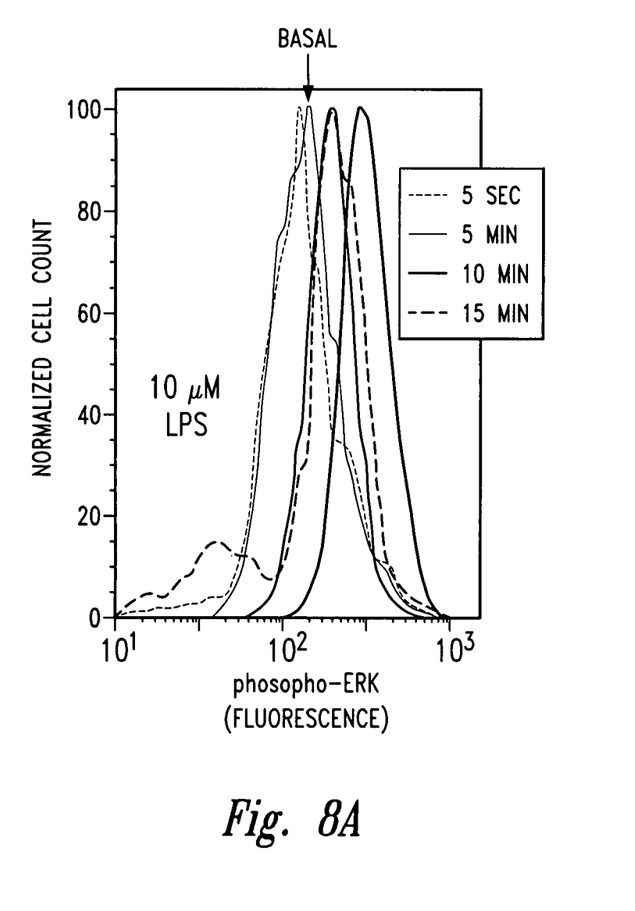
FIGS. 8A-8B depict experimental results for 10 μM LPS stimulation of macrophage cells.
Figure 8B:
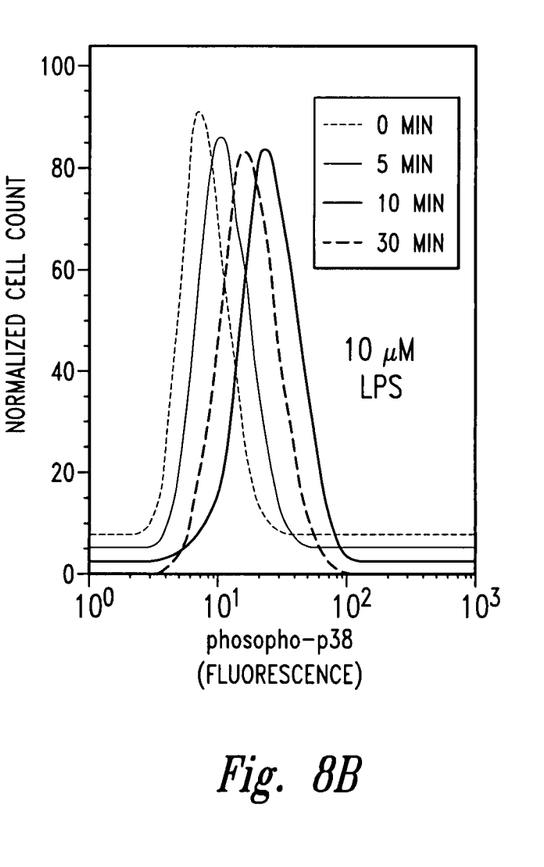

FIGS. 8A-8B depict experimental results for 10 μM LPS stimulation of the macrophage cells. FIG. 8A illustrates normalized cell count vs. fluorescence for ERK1/2. Four traces are shown, for each of four incubation times—5 seconds, 5 minutes, 10 minutes, and 15 minutes, respectively. FIG. 8B illustrates normalized cell count vs. fluorescence for p38, again showing the results of four incubation times—0 minutes, 5 minutes, 10 minutes, and 30 minutes. The relative magnitude of these signals at different times may yield information about the intercellular signaling process.

What is claimed is:

1. A method for performing flow cytometry with imaging, comprising:
   loading a sample fluid containing particles into at least a portion of an incubation chamber on a microfluidic device;
   adding a stimulating agent through to the incubation chamber;
   after an incubation time has elapsed, adding a fixation agent through the incubation chamber of the microfluidic device;
   adding a staining agent through the incubation chamber of the microfluidic device, the staining agent configured to label target analytes of the particles;
   imaging at least a portion of the particles within the incubation chamber;
   transporting the particles to a flow cytometry channel within the microfluidic device;
   exciting the particles with a flow cytometry energy source; and
   receiving energy emitted from the labeled particles with a flow cytometry detector.

2. The method according to claim 1 further comprising:
   after loading the sample fluid, providing stagnant flow within the incubation chamber for a settling time, wherein at least a portion of the particles settle and adhere to a surface of the incubation chamber during the settling time.

3. The method according to claim 2 wherein the act of transporting the particles to the flow cytometry channel comprises detaching at least a portion of the adhered particles from the surface of the incubation chamber.

4. The method according to claim 3 wherein the act of detaching the adhered particles comprises applying a shear force, enzymatic force or a combination of both to the particles using a flow of fluid through the incubation chamber.

5. The method according to claim 1 further comprising, prior to the act of flowing the staining agent through the incubation chamber, transporting at least a portion of the particles to a filter interface.

6. The method according to claim 5 further comprising, after flowing the staining agent through the incubation chamber, releasing the portion of the particles from the filter interface.

7. The method according to claim 1 wherein the particles comprise cells.

8. The method according to claim 1 wherein the incubation chamber comprises a first incubation chamber, the method further comprising:
   loading the sample fluid containing the particles into a second incubation chamber; and
   wherein the act of flowing the stimulating agent through the incubation chamber comprises flowing the stimulating agent through only a selected one or ones of the incubation chambers;
   wherein the act of flowing the fixation agent and staining agent through the incubation chamber comprises flowing the fixation agent and staining agent through the first and second incubation chambers; and
   transporting the particles from the second incubation chamber to the flow cytometry channel while the particles in the first incubation chamber remain in the first incubation chamber.

9. The method according to claim 1 wherein the target analyte comprises a phosphorylated protein.

10. A microfluidic device for integrated flow cytometry, the microfluidic device comprising:
   an incubation chamber;
   a first inlet/outlet port fluidically coupled to the first incubation chamber;
   a second inlet/outlet port fluidically coupled to the first incubation chamber;
   a third inlet/outlet port fluidically coupled to the first incubation chamber;
   a flow cytometry microchannel fluidically coupled to the first incubation chamber;
   a fourth inlet/outlet port fluidically coupled to the flow cytometry microchannel; and
   a fifth inlet/outlet port fluidically coupled to the flow cytometry microchannel; and wherein the incubation chamber is configured to contain particles in a sample fluid, the first and fifth inlet/outlet ports are configured to load the sample fluid into the chamber and flow a staining agent through the incubation chamber to label a target analytes;

wherein the first and third inlet/outlet ports are configured to transport a stimulating agent through the incubation chamber; and wherein the fourth and fifth inlet/outlet ports are configured for fluid flow through the flow cytometry microchannel, including hydrodynamically focused particles, the flow cytometry microchannel configured to receive energy from an excitation source and emit energy from labeled target analytes.

11. The microfluidic device according to claim 10 wherein the incubation chamber is a first incubation chamber, the device further comprising:

a second incubation chamber fluidically coupled to the first incubation chamber; and wherein the incubation chamber is configured to contain particles in a sample fluid, the first and fifth inlet/outlet ports are configured to load the sample fluid into the first and second incubation chambers and flow a staining agent through the first and second incubation chambers to label target analytes.

12. The microfluidic device of claim 11 wherein the first and second incubation chambers each comprise a spiral microchannel.

13. The microfluidic device of claim 10 wherein at least one surface of the first and second incubation chambers comprises quartz.

14. The microfluidic device of claim 10 further comprising a porous filter coupled between the third inlet/outlet port and the first incubation chamber, the third inlet/outlet port configured to supply a vacuum force to draw particles toward the porous filter.

15. The microfluidic device of claim 11 further comprising a first fluidic resistance element between the first inlet/outlet port and the first incubation chamber and a second fluidic resistance element between the first and second incubation chambers.

16. A flow cytometry system comprising:

a microfluidic chip including an incubation chamber and a flow cytometry channel in fluidic communication with the incubation chamber;

a first reservoir configured to contain a sample solution including particles;

a second reservoir configured to contain a stimulating agent;

a third reservoir configured to contain a staining agent, the staining agent configured to label a target analyte;

a fourth reservoir configured to contain a buffer fluid;

the first, second, third, and fourth reservoirs fluidically coupled to the microfluidic device;

at least one electronic pressure pump coupled to the first, second, third, and fourth reservoirs;

a controller coupled to the at least one electronic pressure pump and configured to control the electronic pressure pump and first, second, third and fourth reservoirs to:

flow at least a portion of the sample fluid from the first reservoir into the incubation chamber;

flow at least a portion of the stimulating agent from the second reservoir into the incubation chamber;

provide stagnant flow in the incubation chamber for a predetermined incubation time;

flow at least a portion of the staining agent from the third reservoir into the incubation chamber; and flow particles from the incubation chamber through the flow cytometry channel;

a flow cytometry excitation source configured to couple energy to the flow cytometry channel; and at least one flow cytometry detector configured to receive energy emitted from labeled target analytes in the flow cytometry channel and generate a detection signal.

17. The system according to claim 16 further comprising:

a microscope positioned to image particles in the incubation chamber.

18. The system according to claim 16 further comprising a first valve between the first reservoir and a first inlet/outlet port of the microfluidic device, the controller configured to open the first valve to flow at least a portion of the sample fluid from the first reservoir into the incubation chamber.

19. The system according to claim 18 further comprising a second valve between the second reservoir and a second inlet/outlet port of the microfluidic device, the controller configured to open the second valve to flow at least a portion of the stimulating agent from the second reservoir into the incubation chamber.

20. The system according to claim 16 wherein the predetermined incubation time is less than 15 seconds.

21. The system according to claim 16 further comprising a thermal controller coupled to the microfluidic device.

* * * * *